United States Patent
Schmid-Schonbein et al.

(10) Patent No.: US 8,541,371 B2
(45) Date of Patent: Sep. 24, 2013

(54) TREATMENT OF CONDITIONS RELATED TO CECAL LIGATION SHOCK

(75) Inventors: Geert W. Schmid-Schonbein, Del Mar, CA (US); Frank A. DeLano, San Diego, CA (US)

(73) Assignee: The Regents of The University of California, Oakland, CA (US)

( * ) Notice: Subject to any disclaimer, the term of this patent is extended or adjusted under 35 U.S.C. 154(b) by 247 days.

(21) Appl. No.: 12/989,242

(22) PCT Filed: Apr. 22, 2009

(86) PCT No.: PCT/US2009/041464
§ 371 (c)(1),
(2), (4) Date: Oct. 22, 2010

(87) PCT Pub. No.: WO2009/132149
PCT Pub. Date: Oct. 29, 2009

(65) Prior Publication Data
US 2011/0039781 A1    Feb. 17, 2011

(51) Int. Cl.
*A61K 38/38*    (2006.01)
*C07K 14/76*    (2006.01)

(52) U.S. Cl.
USPC ................... 514/15.2; 514/14.2; 514/15.1

(58) Field of Classification Search
None
See application file for complete search history.

(56) References Cited

U.S. PATENT DOCUMENTS

| 6,534,283 B1 | 3/2003 | Schmid-Shoenbein |
| 2007/0142337 A1 | 6/2007 | Schmid-Schonbein et al. |

FOREIGN PATENT DOCUMENTS

| WO | 2009/045543 A1 | 9/2009 |

OTHER PUBLICATIONS

Schmid-Schonbein and Hugli, A New Hypothesis for Microvascular Inflammation in Shock and Multiorgan Failure: Self-Digestion by Pancreatic Enzymes, 2005, Microcirculation, 12: 71-82.*
Doucet, et al., Inhibition of Enteral Enzymes by Enteroclysis with Nafamostat Mesilate Reduces Neutrophil Activation and Transfusion Requirements after Hemorrhagic Shock. 2004, Trauma, 56(3): 501-511.*
Madan, Use of Ciprofloxacin in the Treatment of Hospitalized Pateints with Intra-abdominal Infections, 2004, Clinical Therapeutics, 26(10): 1564-1577.*
Witek-Janusek and Ratmeyer, Sepsis in the young rat: maternal milk protects during cecal ligation and puncture sepsis but not during endotoxemia, 1991, Circ Shock, 33(4): 200-206.*
The International Bureau of WIPO, International Preliminary Report on Patentability for PCT/US2009/041464, Oct. 26, 2010, see all.
Saha, S.K., "Efficacy of metronidazole lavage in treatment of intraperitoneal sepsis" Digestive Disease and Science, 1996, vol. 41, No. 7, p. 1313-1318.
Penn, A. H. et al. "The intestine as source of cytoxic mediators in shock: free fatty acides and degradation of lipid-binding proteins" Am. J. Physiol. Heart Circ. Physiol. Feb. 8, 2008, vol. 294, H1779-H1792.
Deitch E A, Shi H P, Lu Q, et al. Serine proteases are involved in the pathogenesis of trauma-hemorrhagic shock-induced gut and lung injury. Shock. 2003; 19:452-456.
Fitzal F, DeLano F A, Young C, Schmid-Schonbein G W. Improvement in early symptoms of shock by delayed intestinal protease inhibition. Arch Surg. 2004; 139:1008-1016.
Fitzal F, DeLano F A, Young C, Rosario H S, Junger W G, Schmid-Schonbein G W. Pancreatic enzymes sustain systemic inflammation after an initial endotoxin challenge. Surgery, 134:1-11, 2003.
Muhs B E, Patel S, Yee H, et al. Inhibition of matrix metalloproteinases reduces local and distant organ injury following experimental acute pancreatitis. J Surg Res. 2003; 109 :110-7.
Penn, A H, Hugli, T E, Schmid-Schonbein, G W. Pancreatic enzymes generate cytotoxic mediators in the intestine. Shock 27(3):296-304, 2007.
Rosario H S, Waldo S W, Becker S A, et al. Pancreatic trypsin increases matrix metalloproteinase-9 accumulation and activation during acute intestinal ischemia-reperfusion in the rat. Am J Pathol. 2004; 164:1707-16.
Schmid-Schonbein G W. 2008 Landis Award lecture—Inflammation and the Autodigestion Hypothesis. Microcirculation, 2009; 16:289-306.
Shi H P, Liu Z J, Wen Y. Pancreatic enzymes in the gut contributing to lung injury after trauma/hemorrhagic shock. Chin J Traumatol. 2004; 7:36-41. [abstract].
Wiseman et al., "The Effect of Tranexamic Acid in Fibrin Sealant on Adhesion Formation in the Rat," J Biomed Mater Res Part B: Appl Biomater 68B:222-30, 2004.

* cited by examiner

*Primary Examiner* — Karlheinz R Skowronek
*Assistant Examiner* — Khalid Kader
(74) *Attorney, Agent, or Firm* — Sughrue Mion, PLLC

(57) ABSTRACT

Techniques, methods and lavages are disclosed for prevention or treatment of shock, particularly cecal ligation or cecal inoculation shock, by administering a specific therapeutic agent, which is able to use smaller volumes of reagent to achieve partial to complete inhibition, than other previously described techniques. The agent includes a combination of enzyme inhibitor, cytotoxic lipid binding protein, and antibiotic.

19 Claims, No Drawings

TREATMENT OF CONDITIONS RELATED TO CECAL LIGATION SHOCK

GRANT INFORMATION

This invention was made with government support under Grant No. GM 85072 awarded by the National Institutes of Health. The United States government has certain rights in the invention.

This application is a U.S. national stage application under 35 U.S.C. 371 of the PCT application with Serial No. PCT/US2009/041464, filed Apr. 22, 2009, which claims priority to U.S. Provisional Patent Application Ser. No. 61/047,098, filed Apr. 22, 2008, the contents of all of which are hereby incorporated by reference in their entirety into this disclosure.

BACKGROUND OF THE INVENTION

1. Field of the Invention

The present invention relates to treatment of shock. In particular, the present invention relates to treatment of conditions related to cecal ligation shock.

2. Background of the Invention

Shock is a life-threatening complication in situations associated with trauma including burns, surgery, ischemia, sepsis, radiation and other critical care applications. Shock is a broad term that describes a group of circulatory syndromes, all of which result in general microvascular and cellular dysfunction.

One such result of shock is cell activation, in which studies have shown that cell activation fundamentally alters the biomechanics of microvascular blood flow by a shift in rheological, adhesive, and cytotoxic cell properties. Cellular activation in the circulation can be detected by leukocytes or endothelial cells resulting in superoxide production, pseudopod projections, enzyme release, cytokine release, and expression of membrane adhesion molecules. The condition is typically accompanied by hypoxia, which leads to a depletion of the adenosine triphosphate (ATP), the failure of the sodium-potassium pump, mitochondrial dysfunction, and ultimately the release of a variety of toxic substances, including degrading proteases, superoxides and other oxygen free radicals. Superoxides are toxic to essentially all tissues. They react with proteins and cause unfolding and are able to induce DNA damage. Eventually these stress responses give rise to irreversible cardiovascular collapse because of their combined effects on the microcirculation.

There are few satisfactory drugs, treatment methods, or interventions available for the prevention of conditions related to shock. Most currently available methods for the treatment of such conditions related to shock deal with the symptoms, rather than the cause. For this reason, current clinical approaches are limited in their efficacy and can only prevent further damage from occurring.

Thus, there is a need in the art for a more effective treatment of conditions related to shock. The treatment should be simple to administer, effective and capable of aiding in emergency situations.

SUMMARY OF THE INVENTION

The present invention is a technique for treatment of conditions related to physiological shock, particularly including cecal ligation shock and shock in which cecal material may penetrate the intestinal lumen and/or enter into the peritoneum (cecal inoculum shock), by administering a more specific and potentially smaller combination of therapeutic agents, into the intestine and into peritoneum to achieve complete inhibition, than other previously described methods, for example, that in U.S. Pat. No. 6,534,283, which is incorporated by reference herein in its entirety. The present application also accompanies the findings of co-pending PCT patent application, Serial Number, PCT/US08/11529, filed Oct. 6, 2008, entitled "Treatment of Conditions Related to Shock," and which is incorporated by reference herein in its entirety. The present invention is based upon a new hypothesis for the cause of shock, including cecal inoculum shock, and multi-organ failure: self-digestion through gut ischemic complications rather than bacterial/endotoxin invasion.

In experimental models, it was demonstrated that blockade of pancreatic enzymes in the lumen of the intestine in combination with treatment against cytotoxicity in the peritoneum (blockade of digestive enzymes, binding of cytotoxic mediators and anti-bacterial treatment in the peritoneum) leads to a dramatic enhancement of survival rate in a model of septic shock (cecal ligation model).

Such findings lead to the present invention resulting in treatment techniques for prevention of multi-organ failure and mortality in septic shock associated with punctured intestine, ruptured appendix, or any other situation associated with leakage of intestinal material out of the intestinal lumen (e.g., cecal or fecal matter).

The techniques according to the present invention serve to block inflammation, lesion and tumor formation, and angiogenesis in the intestine, mesentery and other organs in the peritoneal cavity (e.g., in peritonitis). These techniques further dramatically reduce symptoms of multi-organ failure and mortality in cecal inoculum shock associated with leakage of cecal material into the peritoneum (e.g., cecal ligation shock). The techniques have been tested in rats.

In one exemplary embodiment, the present invention is a method for prevention or treatment of cecal inoculum shock. The method includes administering into the peritoneum of an individual a therapeutic dose of a combination of a pancreatic digestive enzyme inhibitor, a cytotoxic lipid (e.g., free fatty acid) binding protein, and an antibiotic.

Among other things, the treatment serves to block autodigestion of peritoneal structures, organ surface protein layers, and the formation of inflammatory mediators by pancreatic digestive enzymes in the intestine in septic shock thereby reducing symptoms of multi-organ failure and significantly reducing mortality rate. It also serves to reduce morbidity and reduce post-operative complications, enhance recovery rate, and shorten hospital stays.

The treatment is administered into the lumen of the intestine to block fully activated digestive enzymes and auto-digestion of the intestine in combination with administration of the treatment into the peritoneum. The combined treatment is highly effective to attenuate prolonged formation of inflammation in cecal inoculum shock and septic shock, destruction of the intestinal epithelial lining, destruction of the intestinal surface layer and the surface layer of other abdominal organs (mesentery, kidney, adrenals, liver, pancreas, aorta and other abdominal organ and tissue structures) and reduces mortality. There is currently no comparable treatment for septic shock.

DETAILED DESCRIPTION OF THE INVENTION

This invention describes techniques for treatment of conditions related to shock. Various exemplary embodiments are presented to provide a broad spectrum of treatment available and application to such conditions.

As discussed above, the strategy for inhibiting gut enteral function has been described in U.S. Pat. No. 6,534,283, which is incorporated by reference herein in its entirety. This patent describes the use of protease inhibition in the lumen of the gut in principle and more specifically using specific commercially available protease inhibitors. The present application also accompanies the findings of co-pending PCT patent application, Serial Number, PCT/US08/11529, filed Oct. 6, 2008, entitled "Treatment of Conditions Related to Shock," and which is incorporated by reference herein in its entirety. The current strategy proposes numerous applications related to treating conditions particularly related to cecal ligation shock.

The present invention provides a novel treatment technique to minimize the formation of peritonitis, intestinal ulcerations, and peritoneal lesion formation with angiogenesis and tumor formation, as would be recognized by one having ordinary skill in the art. This technique provides, among other things, an opportunity for early intervention/prevention of side effects associated with cecal ligation shock.

In the present invention, treatment is administered into the lumen of the intestine in combination with a treatment of the peritoneal cavity that can be administered after onset of shock.

There is currently no generally accepted treatment algorithm or protocol for shock. There is an FDA approved treatment with activated protein C (XIGRIS, drotrecogin alfa (activated), Eli Lilly), which gives a minor but confirmed survival benefit. The inventors are not aware of any preventive diagnosis/treatment of peritonitis and peritoneal lesion formations. Cecal ligation shock is generally treated with saline/buffer lavage of the peritoneal fluid with limited effectiveness.

In an exemplary embodiment, the present invention involves several components, which may be performed independently or in combination. One component of a treatment according to the present invention includes diagnosis of peritoneal fluid for elements of fecal material, pancreatic digestive enzymes and/or inflammatory/cytotoxic mediators (free fatty acids, peptide fragments, gram-positive/gram-negative bacteria, and others).

A second component of a treatment according to the present invention includes a peritoneal lavage with a combination of one or more of: (a) pancreatic protease/lipase inhibitor ((e.g., FUTHAN, nafamostat mesilate (0.45 mM); TRASYLOL, aprotinin, Bayer, 1.4 mg/ml; CYKLOKAPRON, tranemxamic acid (Pfizer), 10 mg/kg) as serine protease inhibitor; orlistat (5 to 50 mg/ml) as lipase inhibitor; plus other pancreatic enzyme inhibitors as known to those skilled in the art); (b) cytotoxic lipid binding protein, such as free fatty acid binding protein (e.g., albumin, Beta-lactoglobulin and others known to those skilled in the art); and (c) antibiotic (e.g., ciprofloxacin, metronidazole, imipenem and cilastatin, ticarcillin and clavulanate, cefuroxime). Treatment for the combination of components may also be administered under conditions of known or expected intestinal leakage (intestinal trauma with puncture, lesions in Crohn's disease, ruptured appendicitis, surgery with open intestines, etc.)

Using the above two component technique, it has been demonstrated that the presence of mixed fecal material in the peritoneal fluid (outside the intestine) leads in experimental animals to peritoneal inflammation, intestinal lesions, polyps, tumor formation and angiogenesis. These forms of pathology are prevented and/or reduced after the peritoneal lavage described above and herein.

Many commercial applications are possible using the above two component technique. For example, it would be possible to develop a diagnostic test to detect early stages of inflammation in the peritoneum from fluid samples. It is also possible to develop a treatment procedure by intestinal lavage to prevent further development of peritonitis and subsequent tumors.

In another exemplary embodiment, the present invention addresses treatment of shock due to cecal inoculum in the peritoneal space ("cecal ligation shock"). Treatment includes administration of an enzyme inhibitor, an antibiotic and a cytotoxic lipid (e.g., free fatty acid) binding protein. Such treatment may take on various forms, including direct injection into the lumen of the intestine (by oral administration, introduction via an esophageal catheter, direct injection into the lumen of the intestine during surgery, etc.). Treatment can also be intravenously (iv) using a protease inhibitor. These various treatment forms may be conducted in conjunction with treatment of the peritoneal space affected by the inoculum with the same enzyme inhibitor, antibiotic and cytotoxic lipid binding protein.

Many different agents may be used in conjunction with this procedure. Enzyme inhibitors include but are not limited to: CYCLOKAPRON, tranexamic acid (10 mg/ml lavage fluid) two times in 6 hours, alpha-1 antitrypsin, (10 mg/ml). Antibacterial treatment against gram-positive and gram-negative bacteria (with antibiotic treatment, e.g., ciprofloxacin, metronidazole, imipenem and cilastatin, ticarcillin and clavulanate, cefuroxime). Free fatty acid binding proteins could include albumin and others. The amount of agent and the concentrations administered are adjusted according to intestine size and peritoneal space to achieve complete blockade of digestive enzyme activity, binding of unbound free fatty acids and bacterial cultures.

The above treatments lead to a highly significant improvement of survival rate in a model of cecal ligation shock by inoculation with 900 mg/kg fecal material directly into the peritoneum. Treatment for prevention of multi-organ failure and mortality in cecal ligation shock (e.g., septic and other forms of shock in patients) associated with punctured intestine, ruptured appendix, or any other situation associated with leakage of intestinal material (cecal or fecal matter). The treatment may also be effective in other forms of shock, due to trauma, burns, radiation and other insults.

In one exemplary embodiment, which may be used for treatment for prevention of post-operational complications, including multi-organ failure, sepsis, morbidity, and mortality, pancreatic protease inhibition is initiated to reduce complications and hospital stay after trauma/surgery. Here, it has been shown that pancreatic enzymes in the intestine have the ability to generate powerful inflammatory mediators and that blockade of pancreatic enzymes in the lumen of the intestine attenuates inflammatory symptoms after different shock models.

In this embodiment, the present invention allows a reduction in inflammatory symptoms and complications (swelling, embolism formation, selected organ dysfunction, pulmonary embolism, incidence of stroke, patient mobility, morbidity, multi-organ failure, mortality) in any form of elective surgery/general anesthesia associated with elevated risks (such as prolonged surgery procedures, surgery with bypass requirements, surgery on patients with preconditions and risk factors, surgery involving the intestine and pancreas, appendectomy). This results in a reduction in post-surgical complications, enhance wound healing, reduce total recovery period, and reduce hospitalization requirements and time.

In elective surgery, pre-administration of a pancreatic enzyme inhibitor may be conducted directly into the lumen of the intestine (by oral administration, introduction via an esophageal catheter, direct injection into the lumen of the intestine during surgery, etc.). The agents to be used are individually or in combination: FUTHAN, nafamostat mesilate (0.1 mM); TRASYLOL, aprotinin (Bayer) (1.4 mg/ml), CYKLOKAPRON, tranexamic acid, serine protease inhibitor; orlistat (5 to 50 mg/ml), lipase inhibitor plus any other pancreatic enzyme inhibitor. The amount administered is adjusted according to intestine size to achieve complete blockade of digestive enzyme activity. The inhibitor is administered prior to general anesthesia/surgery as pretreatment.

It should be noted that the combined treatment with protease inhibition, antibiotic and cytotoxic lipid binding protein (e.g., albumin) could also be used orally in elective surgery.

This is the first intervention against a major source of inflammation in multi-organ failure associated with surgery/general anesthesia. Blockade of digestive enzymes prior to general anesthesia may serve to preserve barrier properties of the intestinal mucosa, reduce inflammation in the central circulation, and consequently reduce recovery and wound healing periods, post-surgical complications, hospital stays, etc.

A potentially important application of the digestive enzyme inhibition as pre-treatment is for patients subjected to radiation or chemotherapeutic treatment. It could also work for radiation treatment under other circumstances to reduce symptoms of multi-organ failure.

In another exemplary embodiment, the present invention provides a method for pancreatic protease inhibition in septic shock. There are many uses for this embodiment, including but not limited to, treatment for prevention of multi-organ failure and mortality in septic shock. Such treatment works by blocking formation of inflammatory mediators by pancreatic digestive enzymes in the intestine in septic shock and thereby reducing symptoms of multi-organ failure and mortality.

The treatment is administered into the lumen of the intestine to block fully activated digestive enzymes and auto-digestion of the intestine. The treatment is highly effective to attenuate prolonged formation of inflammation in septic shock, destruction of the intestinal epithelial lining, and reduces multi-organ failure and mortality.

It is demonstrated that blockade of pancreatic enzymes in the lumen of the intestine attenuates inflammatory symptoms after administration of a lethal dose of endotoxin (6 mg/kg). Experiments demonstrate reduced long-term mortality in the same sepsis model.

Administration of a pancreatic enzyme inhibitor may be conducted directly into the lumen of the intestine (by oral administration, introduction via an esophageal catheter, direct injection into the lumen of the intestine during surgery, etc.). The agents to be used are individually or in combination: FUTHAN, nafamostat mesilate (0.1 mM); TRASYLOL, aprotinin (Bayer) (1.4 mg/ml), CYKLOKAPRON, tranexamic acid, serine protease inhibitor; orlistat (5 to 50 mg/ml), lipase inhibitor; plus any other pancreatic enzyme inhibitor. The amount administered is adjusted according to intestine size to achieve complete blockade of digestive enzyme activity.

In another exemplary embodiment, the present invention is used for pancreatic lipase inhibition to reduce mortality after shock. This embodiment is very useful for developing treatment for prevention of multi-organ failure and mortality in hemorrhagic shock, preventive treatment to reduce the probability for development of multi-organ failure in elective surgery, long-term treatment to reduce production of lipid derived inflammatory mediators associated in chronic diseases. It is also particularly useful because there does not appear to be any treatment proposed to attenuate inflammation by blockade of lipase activity in the intestine in either acute or chronic inflammatory conditions.

This embodiment is designed as an intervention to block the lipase activity in the lumen of the intestine and also in the general circulation in those cases in which lipase enters from the lumen of the intestine into the circulation. This prevents formation of lipid derived inflammatory or cytotoxic mediators in shock and other inflammatory diseases and attenuate multi-organ failure in shock and chronic inflammation in diseases like hypertension, diabetes, the metabolic syndrome, cancers and in chronic degenerative diseases.

Recent evidence resulting in this invention suggests that a major component of inflammatory mediators from the intestine in shock causing multi-organ failure and mortality (e.g., after surgery/general anesthesia, trauma, chronic diseases and any other condition leading multi-organ failure) is derived from the action of pancreatic lipases (lipid splitting enzymes). Blockade of pancreatic lipase serves to reduce mortality during shock and reduce inflammation that leads to multi-organ failure. Blockade of pancreatic lipase prior to general anesthesia may serve to preserve barrier properties of the intestinal mucosa, reduce inflammation in the central circulation, and consequently reduce recovery and wound healing periods, post-surgical complications, hospital stays, etc.

The inventors have shown that the ischemic intestine produces a powerful set of lipid derived cytotoxic mediators and that the blockade of lipase in the intestine under in-vitro conditions blocks the production of lipid-derived cytotoxic mediators.

In elective surgery, pre-administration of a pancreatic enzyme inhibitor directly into the lumen of the intestine (by oral administration, introduction via an esophageal catheter, direct injection into the lumen of the intestine during surgery) is conducted. The agents to be used is individually or in combination: orlistat (5 to 50 mg/ml), lipase inhibitor; plus any other pancreatic enzyme inhibitor. The amount administered is adjusted according to intestine size and content to achieve complete blockade of digestive enzyme activity. As treatment the inhibitor is administered after trauma or sepsis associated with risk for shock and multi-organ failure. As pretreatment the inhibitor is administered prior to general anesthesia/surgery.

The above exemplary embodiments have shown various uses and techniques for decreasing certain conditions related to shock. Thus, as a whole, the present invention is based on data from animal studies that show dramatic reduction in life-threatening shock by inhibiting a body's own aggressive digestive enzymes. This novel approach targets trigger mechanisms in auto-digestion before it launches lethal inflammatory cascade.

Death from heart, lung and kidney failure during shock due to inadequate blood flow can be prevented by an unusual experimental treatment that inhibits the aggressive enzymes that are produced in body to digest food.

The invention provides evidence from recent animal studies that for the first time, studies showed that blockade of the digestive enzymes during shock leads to long-term survival. The results show a dramatic reduction of mortality in hemorrhagic shock induced multi-organ failure. This treatment holds great promise for future clinical application, particularly in emergency rooms and before high-risk surgeries. When a person is in shock, his or her life is on the line. The patient's survival may be in jeopardy not just during surgery, but but also after surgery for periods of days because healthy organs can fail and die in rapid succession.

An estimated 1 million cases of various types of shock are treated annually in U.S. hospital emergency rooms. Shock is a serious medical condition with a fatality rate of approximately 29%. While the optimal management of shock patients can improve survival rates, overall shock remains a condition with a high death rate.

Administering a drug to inhibit the body's digestive enzymes is a relatively new approach that was begun in the past decade. In 1998 a finding was made in laboratory studies on the body's inflammatory cascade and the factors that turn this normal tissue-healing biological process into a virulent, out of control firestorm against the body's normal tissue.

The researchers then began animal studies. The present invention is based on the latest research using rodent models of human hemorrhagic shock. Here it has been discovered that the sudden lowering of blood pressure that occurs in people suffering from trauma, burns, or stroke can provoke the body's powerful digestive enzymes to break down the body's own intestinal tissue as if it were food. Such enzymes' abnormal actions may be defined as "auto-digestion." Auto-digestion is dangerous because not only does it injure healthy tissue but also contributes to multi-organ failure, which can be fatal.

The healthy cells of the animals' intestinal tissue react to auto-digestion by releasing a slew of substances that can be toxic to the heart and other body organs. These substances, termed cytotoxic mediators, can reach these body organs via the blood stream. In their latest studies, different forms of shock were induced in 68 lab rodents, all of which were then treated with therapies that mirror the emergency room care given to many human patients who suffer shock, which typically occurs when blood flow to the heart, lungs and other body organs is slowed as a result of trauma, dehydration, heart attack or stroke.

A total of 33 of the 68 lab rodents in shock were also treated with experimental digestive enzyme inhibitor (6-amidino-2napthyl p-guanidobenzoate dimethane-sulfate (ANGD); CYCLOKAPRON, tranexamic acid), and in the case of cecum inoculation shock with the combination treatment (protease inhibitor, FFA binding protein, antibiotic), 35 rats served as control without the treatment. 29 out of 33 treated rats survived. However, only 8 of the 35 "untreated" animals in shock survived. The other 27 animals died from organ failure within 12 hours. Although these "untreated" animals did not receive the enzyme inhibitors, they were given basic shock care. The enzyme inhibitors dramatically improved the survival rate among the lab animals in which shock had been induced.

In the pig studies, the scientists also are conducting experiments to identify the time period when the experimental treatment will be the most effective in saving lives. The findings will be relevant to the emergency care of human patients in shock. Data indicate that the early the treatment occurs, the better the chances for survival. Current research indicates that the window of opportunity for the treatment to be effective does not seem to be very narrow.

The discovery of the "auto-digestion" process and their positive findings from the experimental treatment ANGD are based on National Institutes of Health funded basic research to determine the origin of the inflammatory cascade that causes organ failure and death. Basically, inflammation is the body's mechanism to repair, to heal tissue. But in shock, the inflammation never stops. It is out of control. Normally the body senses when the inflammatory process has completed the repair after tissue injury and brings it to a halt.

There is little surprise that tissue can be severely damaged by the actions of the body's powerful digestive enzymes, which are secreted by the pancreas but do not become activated until they arrive into the intestine. Digestive enzymes have to be very aggressive, and there has to be lots of them, for efficient digestion, to break down the food that we eat. Normally the intestinal tissue is protected from these enzymes by a layer of secreted mucus and by the tight packing of the cells in the intestinal wall. The enzymes are too big to diffuse between these cells under normal conditions.

The following references, some whose findings are discussed or cited above, are hereby incorporated by reference herein in their entirety into this disclosure:

1. Schmid-Schonbein G W, Hugli T E. A New Hypothesis for Microvascular Inflammation in Shock and Multiorgan Failure: Self-Digestion by Pancreatic Enzymes. *Microcirculation.* 2005; 12:71-82.
2. Doucet J J, Hoyt D B, Coimbra R, et al. Inhibition of enteral enzymes by enteroclysis with nafamostat mesilate reduces neutrophil activation and transfusion requirements after hemorrhagic shock. *J Trauma.* 2004; 56:501-511.
3. Fitzal F, DeLano F A, Young C, Schmid-Schonbein G W. Improvement in early symptoms of shock by delayed intestinal protease inhibition. *Arch Surg.* 2004; 139: 1008-1016.
4. Deitch E A, Shi H P, Lu Q, et al. Serine proteases are involved in the pathogenesis of trauma-hemorrhagic shock-induced gut and lung injury. *Shock.* 2003; 19:452-456.
5. Shi H P, Liu Z J, Wen Y. Pancreatic enzymes in the gut contributing to lung injury after trauma/hemorrhagic shock. *Chin J Traumatol.* 2004; 7:36-41.
6. Muhs B E, Patel S, Yee H, et al. Inhibition of matrix metalloproteinases reduces local and distant organ injury following experimental acute pancreatitis. *J Surg Res.* 2003; 109 :110-7.
7. Rosario H S, Waldo S W, Becker S A, et al. Pancreatic trypsin increases matrix metalloproteinase-9 accumulation and activation during acute intestinal ischemia-reperfusion in the rat. *Am J Pathol.* 2004; 164:1707-16.
8. Fitzal F, DeLano F A, Young C, Rosario H S, Junger W G, Schmid-Schönbein G W. Pancreatic enzymes sustain systemic inflammation after an initial endotoxin challenge. *Surgery,* 134:446-456, 2003.
9. Penn, A H, Hugli, T E, Schmid-Schönbein, G W. Pancreatic enzymes generate cytotoxic mediators in the intestine. *Shock*, in press, 2006.
10. Schmid-Schonbein G W. 2008 Landis Award lecture— Inflammation and the Autodigestion Hypothesis. *Microcirculation,* 2009; 16:289-306.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A method for treatment of cecal ligation shock, the method comprising:
   administering into the peritoneal space of an individual at least a first therapeutic dose and into the lumen of the intestine at least a second therapeutic dose of a combination of a pancreatic digestive enzyme inhibitor, a cytotoxic lipid binding protein, and an antibiotic.

2. The method of claim 1, further comprising:
   diagnosing of peritoneal fluid for elements of fecal material, digestive enzymes and inflammatory/cytotoxic mediators to determine potential for cecal ligation shock.

3. The method of claim 1, wherein the cytotoxic lipid comprises free fatty acid.

4. The method of claim 1, further comprising administering at least a third therapeutic dose of the combination of the pancreatic digestive enzyme inhibitor, the cytotoxic lipid binding protein, and the antibiotic through an intravascular (iv) route.

5. The method of claim 1, wherein the pancreatic digestive enzyme inhibitor comprises a serine protease inhibitor.

6. The method of claim 1, wherein the pancreatic digestive enzyme inhibitor comprises a lipase inhibitor.

7. The method of claim 1, wherein the cytotoxic lipid binding protein comprises albumin.

8. The method of claim 1, wherein the cytotoxic lipid binding protein comprises beta-lactoglobulin.

9. The method of claim 1, wherein the antibiotic comprises one or more of ciprofloxacin, metronidazole, imipenem, cilastatin, ticarcillin, clavulanate, or cefuroxime.

10. A method for treatment of multi-organ failure, the method comprising:
    administering into the peritoneal space of an individual at least a first therapeutic dose and into the lumen of the intestine at least a second therapeutic dose of a combination of a pancreatic digestive enzyme inhibitor, a cytotoxic lipid binding protein, and an antibiotic.

11. The method of claim 10, further comprising:
    diagnosing of peritoneal fluid for elements of fecal material, digestive enzymes and inflammatory/cytotoxic mediators to determine potential for multi-organ failure.

12. The method of claim 10, wherein the cytotoxic lipid comprises free fatty acid.

13. A method for reducing the incidence of mortality in cecal ligation shock, the method comprising:
    administering into the peritoneal space of an individual at least a first therapeutic dose and into the lumen of the intestine at least a second therapeutic dose of a combination of a pancreatic digestive enzyme inhibitor, a cytotoxic lipid binding protein, and an antibiotic.

14. The method of claim 13, further comprising:
    diagnosing of peritoneal fluid for elements of fecal material, digestive enzymes and inflammatory/cytotoxic mediators to determine potential for cecal ligation shock.

15. The method of claim 13, wherein the cytotoxic lipid comprises free fatty acid.

16. The method of claim 1, wherein the pancreatic digestive enzyme inhibitor is selected from the group consisting of bovine pancreatic trypsin inhibitor, nafamostat mesilate, aprotinin, tranexamic acid, and orlistat.

17. The method of claim 10, wherein the pancreatic digestive enzyme inhibitor is selected from the group consisting of bovine pancreatic trypsin inhibitor, nafamostat mesilate, aprotinin, tranexamic acid, and orlistat.

18. The method of claim 13, wherein the pancreatic digestive enzyme inhibitor is selected from the group consisting of bovine pancreatic trypsin inhibitor, nafamostat mesilate, aprotinin, tranexamic acid, and orlistat.

19. A method for treatment of cecal ligation shock, the method comprising:
    administering into the peritoneal space of an individual of at least a first therapeutic dose and through an intravascular (iv) route at least a second therapeutic dose of a combination of a pancreatic digestive enzyme inhibitor, a cytotoxic lipid binding protein, and an antibiotic.

\* \* \* \* \*